United States Patent [19]
Boss et al.

[11] Patent Number: 6,015,479
[45] Date of Patent: Jan. 18, 2000

[54] THIN-LAYER SPECTROELECTROCHEMICAL CELL

[75] Inventors: Pamela A. Boss; Roger D. Boss, both of San Diego, Calif.

[73] Assignee: The United States of America as represented by the Secretary of the Navy, Washington, D.C.

[21] Appl. No.: 08/900,983

[22] Filed: Jul. 25, 1997

[51] Int. Cl.[7] .......................... G01N 21/00; G01N 27/26; G07J 3/00; G07J 3/30
[52] U.S. Cl. ........................................... 204/412; 356/318
[58] Field of Search ........................... 204/412; 356/301, 356/317, 318

[56] References Cited

U.S. PATENT DOCUMENTS

| | | |
|---|---|---|
| H1344 | 8/1994 | Baldauf et al. . |
| 4,037,962 | 7/1977 | Grisar et al. . |
| 4,074,939 | 2/1978 | Rabl . |
| 4,088,407 | 5/1978 | Schoeffel et al. .......................... 356/85 |
| 4,102,573 | 7/1978 | Berstermann . |
| 4,148,612 | 4/1979 | Taylor et al. . |
| 4,195,641 | 4/1980 | Joines et al. . |
| 4,208,129 | 6/1980 | Spencer . |
| 4,267,572 | 5/1981 | Witte . |
| 4,340,303 | 7/1982 | Grisar et al. . |
| 4,620,284 | 10/1986 | Schnell et al. . |
| 4,652,755 | 3/1987 | Solomon et al. . |
| 4,660,151 | 4/1987 | Chipman et al. . |
| 4,719,582 | 1/1988 | Ishida et al. . |
| 4,766,551 | 8/1988 | Begley . |
| 4,801,209 | 1/1989 | Wadlow . |
| 4,802,761 | 2/1989 | Bowen et al. . |
| 4,911,794 | 3/1990 | Parce et al. .......................... 204/412 X |
| 4,971,447 | 11/1990 | Mueller . |
| 5,014,216 | 5/1991 | Stafford et al. . |
| 5,046,846 | 9/1991 | Ray et al. . |
| 5,136,261 | 8/1992 | Lewis . |
| 5,168,323 | 12/1992 | Purtschert et al. . |
| 5,172,192 | 12/1992 | Prather . |
| 5,298,428 | 3/1994 | O'Rourke et al. . |
| 5,335,067 | 8/1994 | Prather et al. . |
| 5,351,198 | 9/1994 | Adachi et al. . |
| 5,379,103 | 1/1995 | Zigler . |
| 5,386,121 | 1/1995 | Barbee et al. . |
| 5,404,218 | 4/1995 | Nave et al. . |
| 5,498,875 | 3/1996 | Obremski et al. . |
| 5,526,121 | 6/1996 | Sandifer et al. . |
| 5,920,385 | 7/1999 | Rossiter .................................... 356/73 |

OTHER PUBLICATIONS

Mosier–Boss et al., "Versitile, Low–Volume, Thin–Layer Cell for in Situ Spectroelectrochemistry", *Analytical Chemistry*, vol. 68, No. 18, pp. 3277–3282. (Sep. 1996).

*Primary Examiner*—Maria Nuzzolillo
*Assistant Examiner*—Jonathan Crepeau
*Attorney, Agent, or Firm*—Harvey Fendelman; Peter A. Lipovsky; Michael A. Kagan

[57] ABSTRACT

An electrochemical cell comprises a cell body having a sample chamber, a working electrode fitted through the cell body and extending into the sample chamber; a counter electrode extending through the cell body into the sample chamber; a reference electrode extending through the cell body into the sample chamber; a window which fits over the cell body; and a cap threaded to the cell body for sealing the window against the cell body. An O-ring fitted between window and the cell body provide a leak proof seal. The cell body may be to made of chemically resistant material and be small enough to fit inside the sample chamber of a spectrometer. An O-ring interposed between the cell body and window provides a leak-tight seal, obviating the need for epoxy cement or other sealing compounds so that the cell may be easily disassembled. The cell may be used to monitor electrochemical reactions of moisture and oxygen sensitive materials, as well as electrochemical reactions of corrosive materials.

9 Claims, 3 Drawing Sheets

THIN-LAYER SPECTROELECTROCHEMICAL CELL

BACKGROUND OF THE INVENTION

The present invention generally relates to the field of spectroelectrochemistry, and more particularly, to a spectroelectrochemical cell for performing in situ spectroelectrochemical analysis.

Because of their high theoretical energy densities, the thionyl chloride catholytes have attracted a great deal of attention. However, development of safe Li/SOCl$_2$ batteries capable of operating at high theoretical energy and power densities requires an understanding of the mechanism of electroreduction. Such studies are difficult to undertake since thionyl chloride solutions of AlCl$_3$ and LiCl are very corrosive as well as moisture sensitive. Consequently, considerable care must be exercised in designing the appropriate experimental procedures and apparatus to conduct these studies. For example, in previous studies of the electroreduction of these electrolytes, infrared spectra were obtained from electrolytes sampled during discharge. Conventional infrared liquid cells were used. Consequently, it was not possible to determine what reactions were actually occuring near the electrode surface. Because of the large path lengths, the solutions were strongly absorbing and the spectra obtained were often clipped. The spectra also showed evidence of water contamination as shown by the bands at 3400 cm$^{-1}$, due to AlCl$_3$OH$^-$, and 2900 cm$^{-1}$, due to HCl.

Therefore, a need exist for an electrochemical cell by which it may be determined what chemical reactions occur at the surface of the electrode, and which prevents water from contaminating the electrolyte. Determining the chemical reactions the occur at the surface of the electrode is important in order to monitor and control the chemical reactions taking place.

SUMMARY OF THE INVENTION

The present invention provides an electrochemical cell which comprises a cell body having a sample chamber; a working electrode fitted through the cell body and extending into the sample chamber; a counter electrode extending through the cell body into the sample chamber; a reference electrode extending through the cell body into the sample chamber; a window which fits over the cell body; and a cap threaded to the cell body for securing the window against the cell body. An O-ring fitted between the window and the cell bodyprovides a leak-tight seal. The cell body may be made of chemically resistant material and be small enough to fit inside the sample chamber of a spectrometer. Moreover, the distance between the tip of the working electrode and the inside of the window may be varied, although each set of measurements is generally carried out at a fixed distance. The use of an O-ring between the cell body and window provides a leak-tight seal, obviating the need for epoxy cement or other sealing compounds so that the cell may be easily disassembled. The cell may be used to monitor electrochemical reactions of moisture and oxygen sensitive materials, as well as electrochemical reactions of corrosive materials.

The electrochemical cell may also be incorporated into a spectroelectrochemical analysis system which comprises an electrochemical cell; a laser for generating a laser beam; a first optical fiber for directing the laser beam onto the electrochemical cell; a second optical fiber for collecting optical signals emitted and reflected from the electrochemical cell; a spectrograph for dispersing the optical signals; a charge coupled device which generates electrical signals in response to receiving the dispersed optical signals from the spectrograph; and a computer for analyzing the electrical signals generated by the charge coupled device.

The electrochemical cell may also be incorporated into a spectral absorption analysis system which comprises an electrochemical cell having working, reference, and counter electrodes; a potentiostat for establishing voltage potentials at the working, reference, and counter electrodes; a broadband light source which irradiates the electrochemical cell with a broadband light signal; a photodetector for detecting optical signals from the electrochemical cell; and a computer for analyzing digital representations of the optical signals received by the computer.

BRIEF DESCRIPTION OF THE DRAWINGS

Throughout the several views, like elements are referenced using like references.

DESCRIPTION OF THE PREFERRED EMBODIMENT

Figure 1:
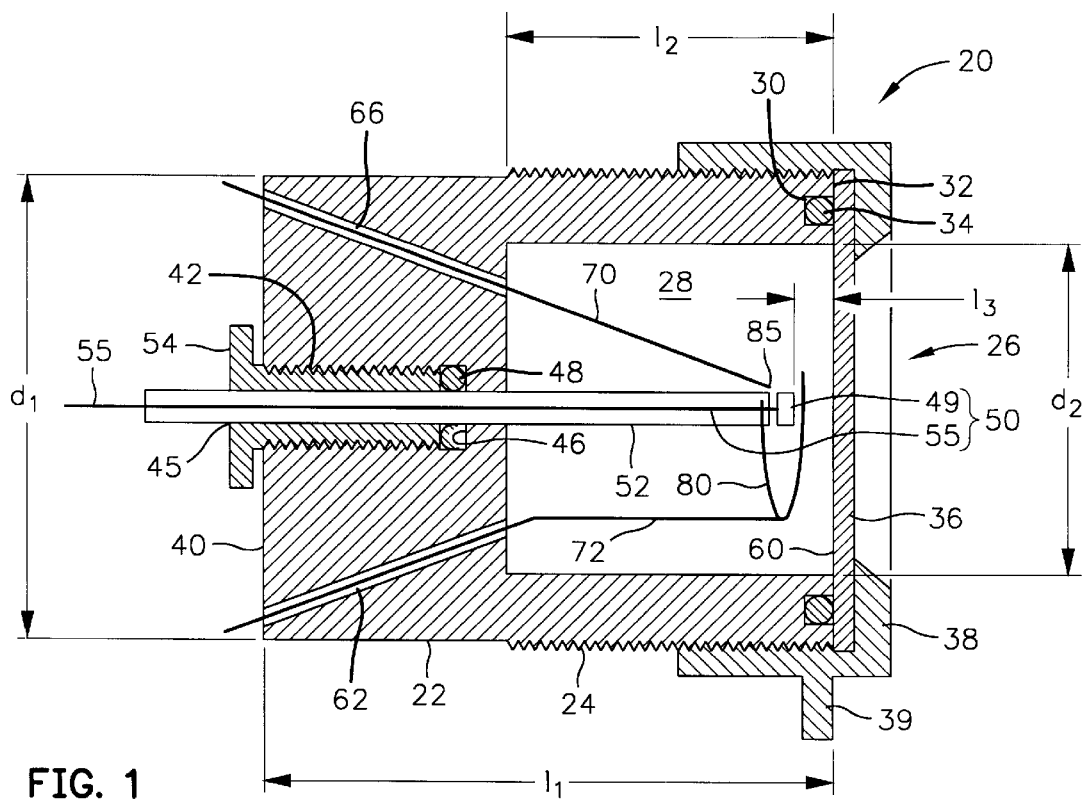
FIG. 1 is a cross-sectional view of an electrochemical cell embodying various features of the present invention.
Figure 2:
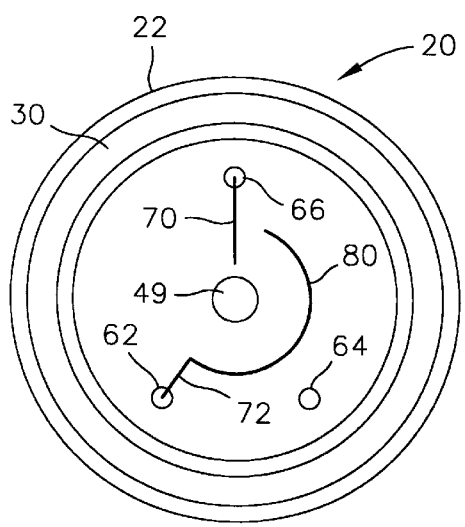
FIG. 2 is a front view of the electrochemical cell of FIG. 1.

Referring to FIGS. 1 and 2, there is shown an electrochemical cell 20 having a cell body 22 preferably constructed from a cylinder of machinable glass ceramic, such as MACOR® by Dow Chemical and may, for example, have a diameter, $d_1$, of about 26 mm and a length, $l_1$, of about 25 mm. Machinable ceramic was selected for the material for cell body 22 because of its rigidity, ease in machining, and chemical resistant properties. A fine thread 24 is formed on the outside of the cell body 22 which extends from the observation end 26 of the body 22. A sample chamber 28 for holding an analyte of interest is formed in the cell body 22, as for example, by machining a hollow, concentric cylinder having, exemplified by a diameter, $d_2$, of about 15 mm and a length, $l_2$, of about 13 mm. A circular groove 30 is formed in the ridge 32 of the cell body 22 in which is fitted an O-ring 34 which may have an 18.7 mm inner diameter, and be 2.6 mm wide. The O-ring 34 is preferably formed of a material having chemical resistance to the analyte of interest. For example, KALREZ® O-rings by DuPont have been found suitable where thionyl chloride has been the analyte. KALREZ® O-rings have excellent chemical resistance, thermal stability, and resistance to swelling and embrittlement, and therefore, may be used in hot, corrosive environments. Window 36 is held in place against the cell body 22 at observation end 26 by window retainer cap 38 which is threaded to threads 24 of cell body 22 so that the O-ring 34 is compressed between the window 36 and the cell body 22, thereby providing a generally leak-tight seal. The window retainer cap 38 may include a flange 39 by which the cell 20 may be supported in a clamp when the window retainer cap 38 is mounted to the cell body 22.

The backside 40 of the cell body 22 opposite the sample chamber 28 has a threaded aperture 42 which may be about 9 mm in diameter and extend part way through the backside 40. A pass hole or aperture 44 having a diameter, for example, of about 5 mm, is formed in the backside 40 of the cell body 22 so that the pass hole 44 is coaxially aligned coterminous with threaded aperture 42. The junction of the pass hole and threaded aperture provides an annular land 46 for receiving an O-ring 48, preferably having the same chemical and other physical properties of O-ring 34.

A disk or rod-shaped electrically conducting working surface 49 is mounted and electrically coupled to the end of an electrically conducting wire lead 55. The working surface 49 and wire lead 55 collectively comprise a working electrode 50. The conducting wire lead 55 is mounted within a tube 52, made of a material preferably having high electrical impedance, such as glass. The working surface 49 is positioned beyond the end of the tube 52 towards the window 36 so that it may be exposed to analyte in the sample chamber 28. The tube 52 is fitted through the center bore 45 of externally threaded bushing 54, preferably made of TEFLON®, whereupon O-ring 48 is fitted over the end of the tube fitted through threaded aperture 42. The bushing 54 then is threaded within the threaded aperture 42 so that O-ring 48 is seated against the annular land 46 to provide a leak-tight seal between the tube 52 and the cell body 22. The working electrode 50 may be made of polished foil and sealed within the tube 52 using a chemically resistant epoxy such as EPOXY PATCH C®, by Hysol Corporation. The working electrode 50 could also be shrouded in TEFLON® or KEL-F®. Ohmic contact to the working electrode 50 and wire lead 55 may be facilitated using an electrically conductive epoxy. An important feature of the spectroelectrochemical cell 20 is that the distance, $l_3$, between the working surface 49 and the interior surface 60 of window 36 may be adjusted to suit the requirements of a particular application.

Figure 3:
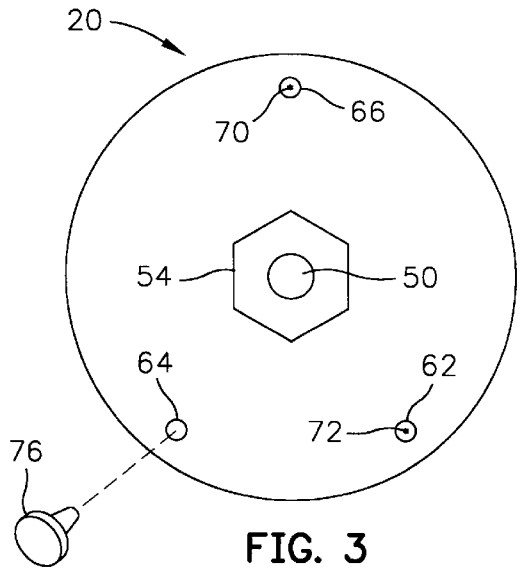
FIG. 3 is a back view of the electrochemical cell of FIG. 1.

Referring to FIGS. 2 and 3, holes 62, 64, and 66, which may be about 2–3 mm in diameter, are formed in the backside 40 of cell body 22 and may be positioned about 120 degrees apart near the periphery of the cell body 22. Reference electrode 70, may be made of Ag/AgCl and fitted through hole 66. Counter electrode 72, which may be formed of Pt, is fitted through hole 62. The holes 62 and 66 preferably are sealed with chemically resistant epoxy, such as described above, or may be mounted in TEFLON® collets, not shown, which are threaded into the holes 62 and 66. The remaining hole 64 is used as a fill hole in which analyte may be introduced into the sample chamber 28. A TEFLON® plug 76 seals the hole 64.

Figure 4:
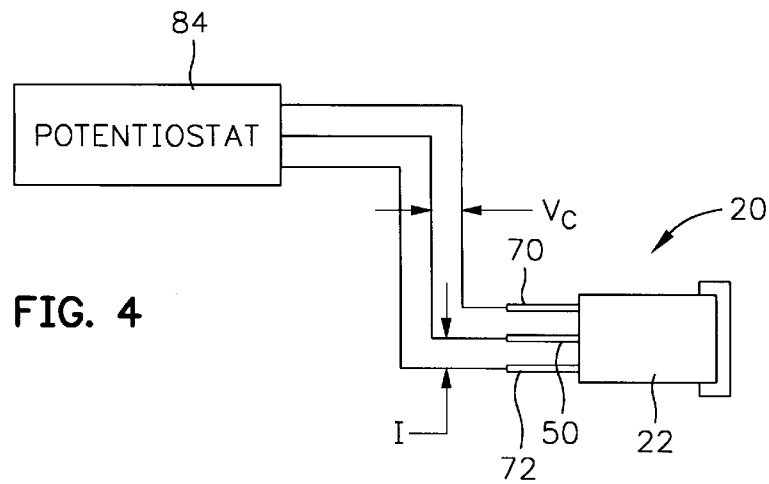
FIG. 4 shows a potentiostat connected to the electrodes of the electrochemical cell of FIG. 1.

Referring to FIGS. 1 and 2, counter electrode 72 has a generally semicircular section 80 positioned in a spaced relation around the working surface 49. The tip 85 of reference electrode 70 is separated slightly from the working surface 49. Then the fill hole 64 is sealed with plug 76. The reference electrode 70, counter electrode 72, and working electrode 50 are electrically connected to a potentiostat 84, as shown in FIG. 4. A constant voltage potential, V, is maintained between the reference electrode 70 and the working electrode 50, and current, I, flows between the working electrode 50 and the counter electrode 72. By way of example, the potentiostat may be implemented as a PAR Model 173. The voltage level V is established to suit the requirements of a particular application.

The spectroelectrochemical cell 20 easily fits within the sample chamber of a spectrometer and requires greatly reduced sample volume, for example, less than 5 milliliters, and may even be on the order of about 1–2 milliliters. A variable distance, $d_3$, between the inside surface 60 of the sample window 36 and the working surface 49 is possible, although in most applications, the distance $d_3$ is held constant. The leak tight seal provided by O-ring 34 fitted between window 36 and the cell body 22 does not require the use of epoxy cement or other chemical contamination. Because the cell 20 is leak tight, it may be used to monitor electrochemical reactions of moisture and oxygen sensitive materials. Moreover, since the cell 20 is made of chemically resistant materials, it may be used to monitor electrochemical reactions of corrosives. The cell 20 may be easily disassembled, which facilitates cleaning and replacement of cell components.

Figure 5:
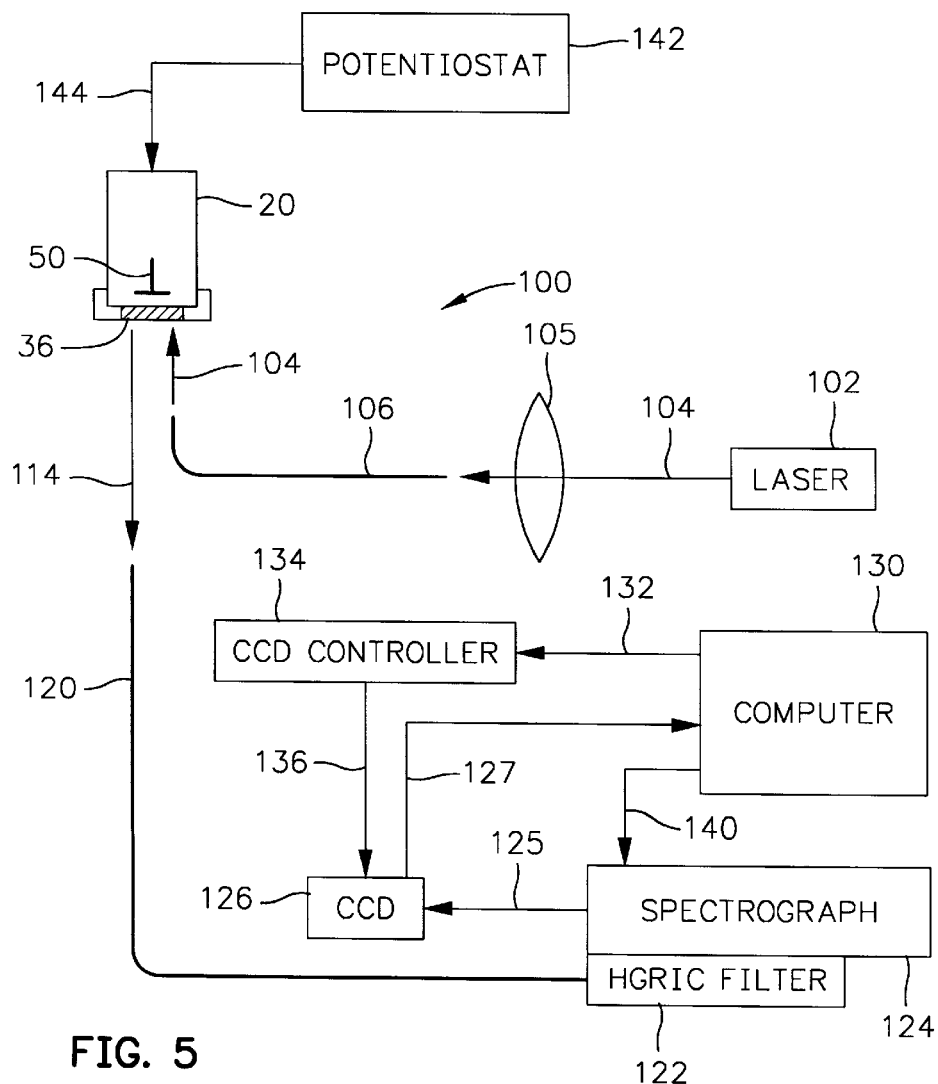
FIG. 5 is a block diagram of a spectral analysis system which incorporates the electrochemical cell of FIG. 1.

An example of an application wherein the spectroelectrochemical cell 20 is used in a system for performing spectral emissions analysis is described with reference to FIG. 5. Referring to FIG. 5 there is shown spectroelectrochemical analysis system 100 which includes laser 102 which generates a laser beam 104 that is focused by lens 105, such as a 5× microscopic lens, before being injected into optical fiber 106. By way of example, the laser 102 may be a tunable CW laser diode such as a Spectra Diode Laser, SDL-8630. The laser beam 104 propagates through optical fiber link 106 and is ejected to irradiate the working surface 49 of the spectroelectrochemical cell 20 through window 36. Potentiostat 142, such as a PAR Model 173, provides suitable voltage controls signal 144 to the electrodes of cell 20. Optical signal 114 from cell 20 includes spectral emissions generated by electrochemical reactions in the analyte contained within cell 20 are received by optical fiber link 120 and are directed through holographic notch filter 122 which rejects the Raleigh line from the laser 102. The notch filter 122 may be a Kaiser Optical Systems Part No. HNF-777-1.0. The optical signal 114 is dispersed and transformed by spectrograph 124 into dispersed optical signals 125. The spectrograph may be a Chromex Raman One imaging spectrograph with a 250 mm focal length. The dispersed spectral emissions 125 are detected and transformed by CCD camera 126 into electrical output signals 127 which are provided to computer 130 for further analysis. An example of a CCD camera suitable for use in conjunction with the present invention is a Princeton Instruments thermoelectrically cooled charge-coupled detector having a 1152 by 298 diode array chip, and controller, Model TE/CCD-1153EM with ST 130. The computer 130 may be a PC-based, PENTIUM® type personal computer which provides CCD output control signals 132 to CCD controller 134. CCD controller 134 generates operation control signals 136 which direct the operation of CCD camera 126. The operation of spectrograph 124 is controlled by computer 130 via signal 140.

Figure 6:
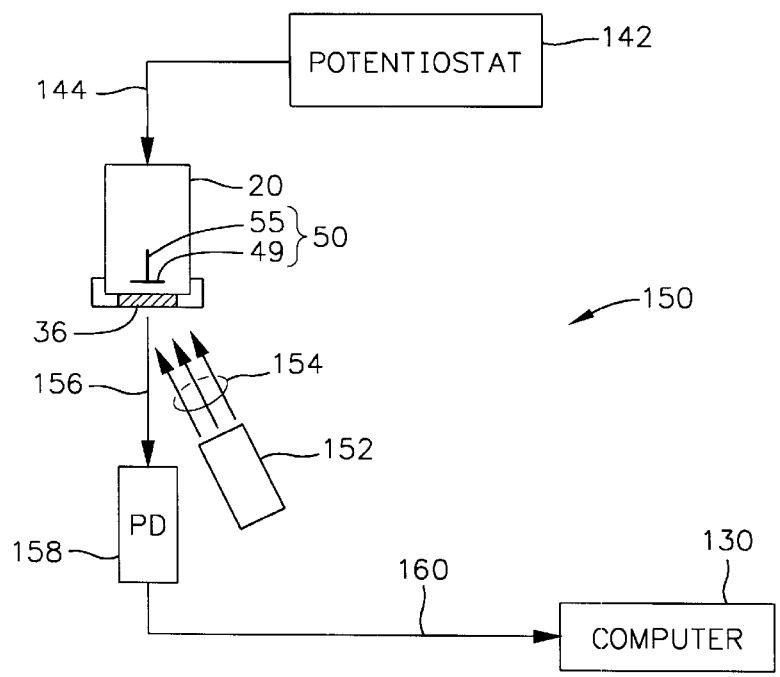
FIG. 6 is a block diagram of a spectral absorption analysis system which incorporates the electrochemical cell of FIG. 1.

An example of a system 150 for performing absorption spectrum analysis in which spectroelectrochemical cell 20 is used is described with reference to FIG. 6. Referring to FIG. 6, absorption spectrum analysis system 150 includes potentiostat 142, electrochemical cell 20, broadband light source 152, photodetector 158, and computer 130. In the operation of absorption spectrum analysis system 150, electrochemical cell 20 is filled with an analyte of interest as described above. Electrochemical reactions are induced in the analyte by applying appropriate voltage control to the working, reference, and counter electrodes 50, 70, and 72, respectively, with signals 144 generated by potentiostat 142. Broadband light source 152, such as a globar, generates broadband light signals 154 that are directed through window 36 to working surface 49 of working electrode 50 and irradiate the analyte in electrochemical cell 20 (FIG. 1). Light signals 156 reflected off the analyte are detected by photodetector 158, such as a photodiode. The photodiode 158 generates a signal 160 which represents the spectrum of light signal 156. Computer 130 receives the light signal from photodetector 158. A software routine implemented in computer 130 subtracts a value representing a reference optical signal from a digitized value representing signal 160 to determine which wavelengths present in the reference optical signal are not present in signal 156. The reference optical signal may be obtained by having photodetector 158 detect light reflected from the analyte in electrochemical cell 20 when the broadband light source 152 is turned off.

Figure 7:
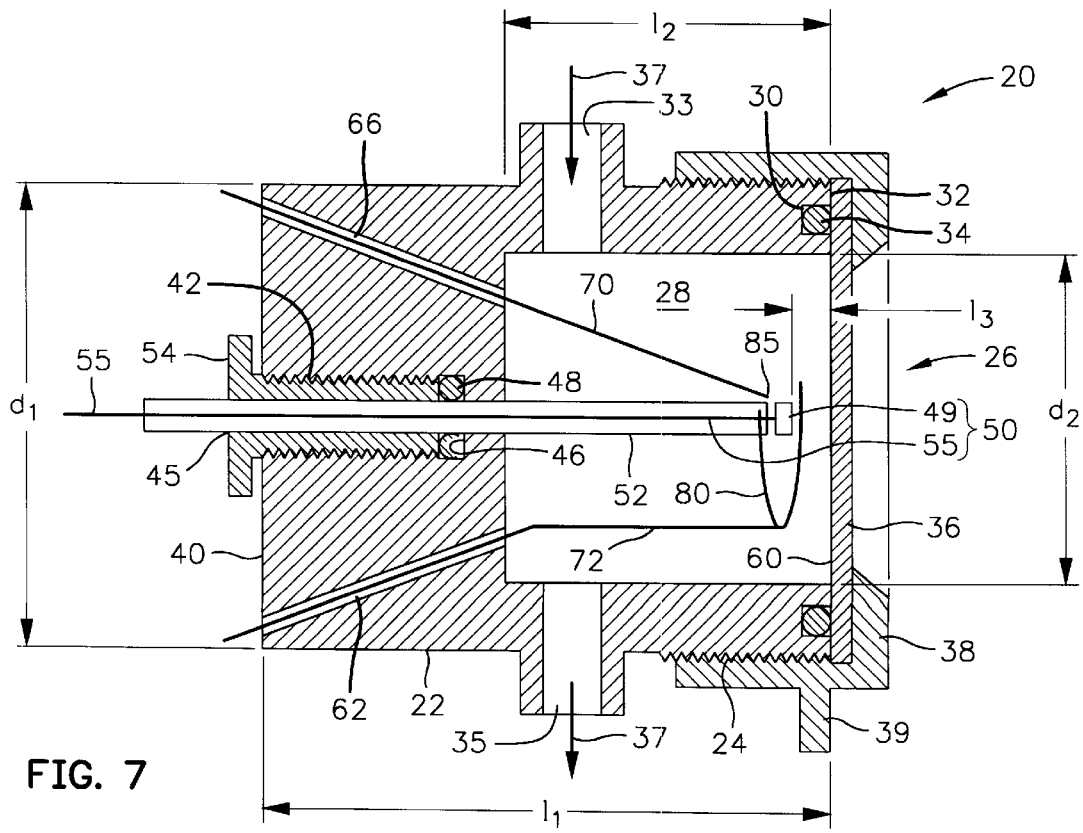
FIG. 7 is a cross-sectional view of an electrochemical cell embodying various features of the present invention which further includes inlet and outlet ports interconnected to the sample chamber.

In FIG. 7, there is shown another embodiment of electrochemical cell 20 which further includes inlet port 33 through which analyte 37 may enter the sample chamber 28, and an outlet port 35 from which the analyte may exit the sample chamber 28. The inlet and output ports 33 and 35, respectively, allow the electrochemical cell 20 to be used in a system for monitoring and controlling electrochemical processes.

Obviously, many modifications and variations of the present invention are possible in light of the above teachings. It is therefore to be understood that within the scope of the appended claims, the invention may be practiced otherwise than as specifically described.

We claim:

1. An electrochemical system, comprising:
   an electrochemical cell which includes:
      a cell body having a sample chamber;
      a working electrode extending through said cell body into said sample chamber,
      a counter electrode extending through said cell body into said sample chamber;
      a reference electrode extending through said cell body into said sample chamber;
      a window; and
      a cap for sealing said window against said cell body.

2. The electrochemical system of claim 1 wherein said cell body consists essentially of a machinable ceramic material.

3. The electrochemical system of claim 1 wherein said window consists essentially of a material selected from the group of quartz, glass, and sapphire.

4. The electrochemical system of claim 1 which includes a first O-ring interposed between said window and said cell body.

5. The electrochemical system of claim 4 wherein said cell body includes:
   a pass through bore extending into said sample chamber and having a first diameter;
   a threaded bore having a second diameter and extending from the exterior of said cell body and which is coaxially aligned and coterminous with said pass through bore to form an annular land;
   a threaded bushing threaded within said threaded bore and having a center bore;
   a tube made of an electrically insulating material in which said working electrode is fitted, and which fits within said center bore of said threaded bushing, and said pass through bore; and
   a second O-ring fitted over said tube which abuts said annular land for providing a seal between said tube and said cell body.

6. The electrochemical system of claim 1 wherein said sample chamber has a volume less than about 5 milliliters.

7. The electrochemical system of claim 1 wherein said cell body further includes inlet and output ports for providing fluid communication to sample chamber.

8. The electrochemical system of claim 1 further including:
   a laser for generating a laser beam;
   a first optical fiber for directing said laser beam to irradiate said electrochemical cell;
   a second optical fiber for collecting optical signals emitted and reflected from said electrochemical cell;
   a spectrograph for dispersing said optical signals;
   a charge coupled device which generates electrical signals in response to receiving said dispersed optical signals from said spectrograph; and
   a computer which analyzes said electrical signals generated by said charge coupled device.

9. The electrochemical system of claim 1 further including:
   a potentiostat for establishing voltage potentials at said working, reference, and counter electrodes;
   a broadband light source which irradiates said electrochemical cell with a broadband light signal;
   a photodetector for detecting optical signals from said electrochemical cell; and
   a computer for analyzing digital representations of said optical signals received by said computer.

* * * * *